United States Patent
Iimura et al.

(10) Patent No.: US 6,906,083 B2
(45) Date of Patent: Jun. 14, 2005

(54) 4-SUBSTITUTED PIPERIDINE COMPOUND

(75) Inventors: Yoichi Iimura, Ibaraki (JP); Takashi Kosasa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/296,379

(22) PCT Filed: Jun. 21, 2001

(86) PCT No.: PCT/JP01/05320

§ 371 (c)(1),
(2), (4) Date: Nov. 25, 2002

(87) PCT Pub. No.: WO01/98271

PCT Pub. Date: Dec. 27, 2001

(65) Prior Publication Data

US 2003/0166925 A1 Sep. 4, 2003

(30) Foreign Application Priority Data

Jun. 21, 2000 (JP) .......................................... 2000-186085

(51) Int. Cl.[7] .................... A61K 31/445; C07D 211/06; C07D 211/32
(52) U.S. Cl. ........................ 514/319; 546/205; 546/206
(58) Field of Search .......................... 514/319; 546/205, 546/206

(56) References Cited

U.S. PATENT DOCUMENTS

| | | | |
|---|---|---|---|
| 5,100,901 A | 3/1992 | Sugimoto et al. ............ | 514/319 |
| 6,277,866 B1 | 8/2001 | Takeuchi et al. ............. | 514/319 |
| 6,677,330 B1 * | 1/2004 | Iimura et al. ................ | 514/183 |
| 2002/0177593 A1 | 11/2002 | Ishihara et al. ........... | 514/227.5 |
| 2004/0048893 A1 | 3/2004 | Lerman et al. .............. | 514/319 |

FOREIGN PATENT DOCUMENTS

| | | |
|---|---|---|
| EP | 0 602 424 A1 | 6/1994 |
| JP | 9-268176 A | 10/1997 |
| JP | 2000-319257 A | 11/2000 |
| WO | 92/17475 A1 | 10/1992 |
| WO | WO 00/18391 A1 | 4/2000 |
| WO | WO 00/51985 A1 | 9/2000 |
| WO | WO 00/57880 A1 | 10/2000 |
| WO | WO 02/02526 A1 | 1/2002 |

OTHER PUBLICATIONS

Wilbraham et al. "Introduction to organic and biological chemistry" S. III. Univ. press p. 268–269 (1984).

* cited by examiner

*Primary Examiner*—Celia Chang
(74) *Attorney, Agent, or Firm*—Birch, Stewart, Kolasch & Birch, LLP

(57) ABSTRACT

The present invention provides a novel compound having a superior acetylcholinesterase inhibitory action. It provides a compound represented by the formula:

(I)

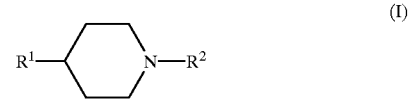

(In the formula, $R^1$ represents a group represented by the formula:

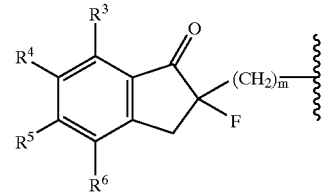

(wherein, $R^3$, $R^4$, $R^5$ and $R^6$ are the same as or different from each other and each represents a hydrogen atom, an optionally substituted $C_{1-6}$ alkoxy group and the like; and m represents an integer from 0 to 6) and the like; and $R^2$ represents a hydrogen atom, an optionally substituted $C_{1-6}$ alkyl group, an optionally substituted $C_{2-6}$ alkenyl group or an optionally substituted $C_{2-6}$ alkynyl group), a salt thereof or a hydrate of them.

19 Claims, No Drawings

4-SUBSTITUTED PIPERIDINE COMPOUND

This application is the national phase under 35 U.S.C. § 371 of PCT International Application No. PCT/JP01/05320 which has an International filing date of Jun. 21, 2001, which designated the United States of America.

FIELD OF THE INVENTION

The present invention relates to a novel compound useful as an acetylcholinesterase inhibitor, a salt thereof or a hydrate of them, and to a process for producing it.

PRIOR ART

It has been known that senile dementia such as Alzheimer-type senile dementia, cerebrovascular dementia, attention deficit hyperactivity disorder and the like are accompanied by a reduction in cholinergic functions in the brain. At present, it has been recognized that acetylcholinesterase inhibitors are effective as an agent for treating these diseases, and actually, they have been clinically applied. In addition to its typical therapeutic agent, Donepezil Hydrochloride (1-benzyl-4-[(5,6-dimethoxy-1-indanon)-2-yl] methylpiperidine hydrochloride), for example, Rivastigmine (3-[1-(dimethylamino)ethyl]phenyl N-ethyl-N-methylcarbamate), Metrifonate (dimethyl (2,2,2-trichloro-1-hydroxyethyl)phosphate), Tacrine Hydrochloride (1,2,3,4-tetrahydro-9-acridinamine), Galanthamine Hydrobromide, Neostigmine and Physostigmine are known.

However, among the above-mentioned therapeutic agents, Donepezil Hydrochloride is the only one that has been actually clinically applied and has been recognized as useful in points of pharmacological activities against the disease, side effects, administrations times, administration forms etc. Further, except for this agent, no acetylcholinesterase inhibitors being clinically useful have been found. Therefore, there have been strong demands for useful acetylcholinesterase inhibitors having superior effects other than Donepezil Hydrochloride.

DISCLOSURE OF THE INVENTION

Under such circumstances, the present inventors have extensively studied for a long period of time. As a result, they have successfully synthesized a novel compound represented by the formula:

(I)

in the formula, $R^1$ represents any one of group selected from the group consisting of the formulae:

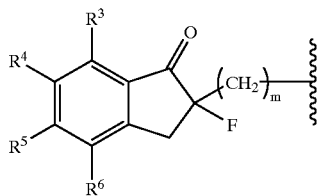

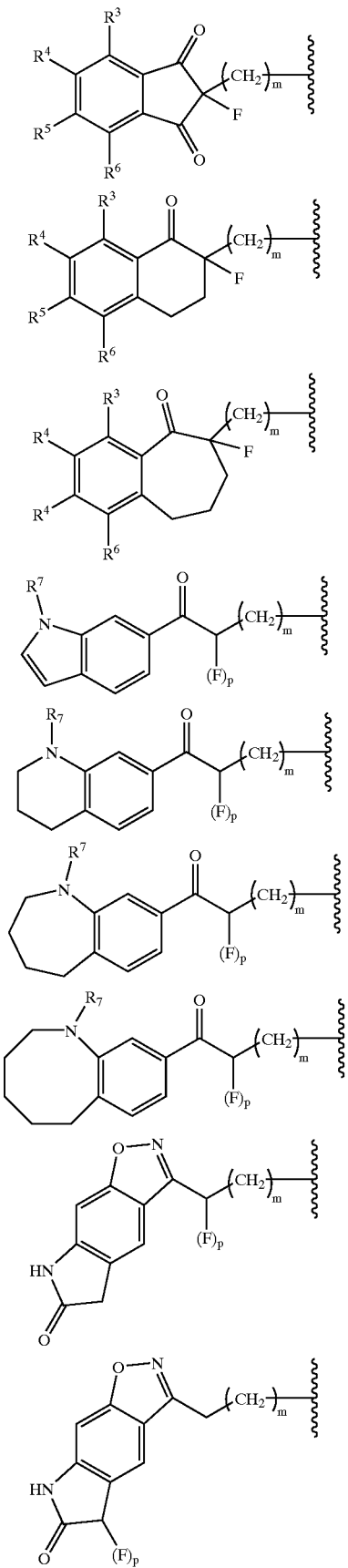

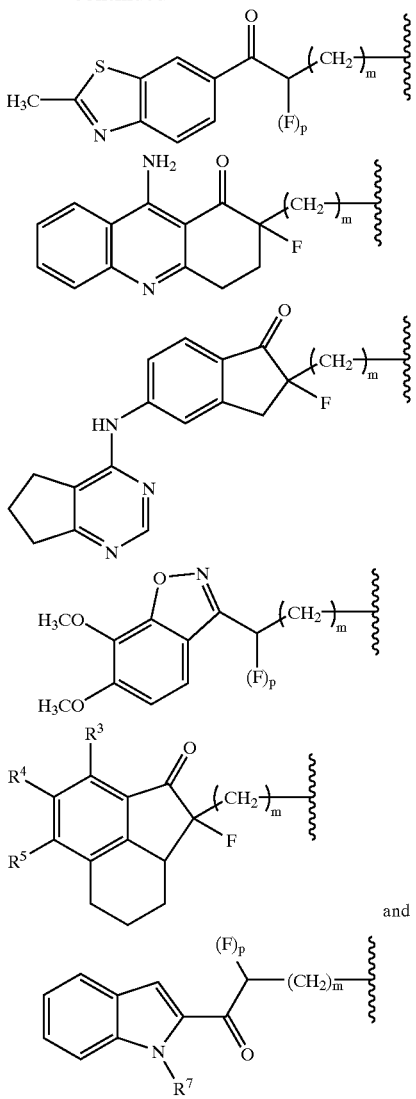

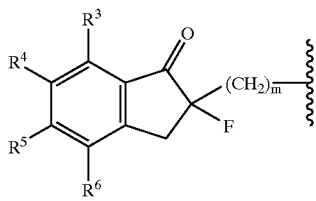

(in the formulae, $R^3$, $R^4$, $R^5$ and $R^6$ are the same as or different from each other and each represents a hydrogen atom, a halogen atom, a hydroxyl group, an optionally substituted hydrocarbon group, an optionally substituted $C_{1-6}$ alkoxy group, a $C_{1-6}$ acyl group, a nitro group, an optionally substituted amino group, an optionally substituted amide group, a mercapto group or a $C_{1-6}$ thioalkoxy group; $R^7$ represents a hydrogen atom or a $C_{1-6}$ alkyl group; a bond represented by the partial structure ═ may be a single bond or a double bond; m is 0 or an integer from 1 to 6; and p represents an integer of 1 or 2); and $R^2$ represents a hydrogen atom, an optionally substituted $C_{1-6}$ alkyl group, an optionally substituted $C_{2-6}$ alkenyl group or an optionally substituted $C_{2-6}$ alkynyl group. Further, they have found unexpectedly that the compound, a salt thereof and a hydrate of them have a superior acetylcholinesterase inhibitory action, and make it possible to achieve the initial objective. Thus, they have accomplished the present invention.

That is, the present invention relates to (1) a compound represented by the above formula (I), a salt thereof or a hydrate of them. Further, (2) in the above-mentioned (1), $R^1$ may be a group represented by the formula:

hydrate of them. Further, (2) in the above-mentioned (1), $R^1$ may be a group represented by the formula:

(in the formula, $R^3$, $R^4$, $R^5$, $R^6$ and m are have the same meanings as defined in the above-mentioned (1)); (3) in the above-mentioned (1) or (2), $R^3$, $R^4$, $R^5$ and $R^6$ may be the same as or different from each other and each may be a hydrogen atom or an optionally substituted $C_{1-6}$ alkoxy group; (4) in the above-mentioned (1) or (2), $R^3$, $R^4$, $R^5$ and $R^6$ may be the same as or different from each other and each may be a hydrogen atom or an optionally substituted methoxy group; (5) in the above-mentioned (1) or (2), m may be an integer of 1; (6) in the above-mentioned (1), $R^1$ may be [(5,6-dimethoxy-2-fluoro-1-indanon)-2-yl]methyl group; (7) in the above-mentioned (1) or (2), $R^2$ may be a hydrogen atom; (8) in the above-mentioned (1) or (2) , $R^2$ may be an optionally substituted $C_{1-6}$ alkyl group; (9) in the above-mentioned (1) or (2), $R^2$ may be a $C_{1-6}$ alkyl group which may be substituted with 1) a halogen atom, 2) a hydroxyl group or 3) a nitrile group; (10) in the above-mentioned (1) or (2), $R^2$ may be a methyl group, an ethyl group, a n-propyl group, an iso-propyl group, a 2-methyl-1-propyl group or a tert-butyl group; and (11) in the above-mentioned (1), the compound may be 4-[(5,6-dimethoxy-2-fluoro-1-indanon)-2-yl]methylpiperidine, 4-[(5,6-dimethoxy-2-fluoro-indanon)-2-yl]methyl-1-methylpiperidine, 4-[(5,6-dimethoxy-2-fluoro-1-indanon)-2-yl]methyl-1-(1-methylethyl)piperidine or 4-[(5,6-dimethoxy-2-fluoro-1-indanon)-2-yl]methyl-1-(2-methylpropyl)piperidine. Moreover, the present invention relates to (12) a medicine comprising the compound described in the above-mentioned (1) a salt thereof or a hydrate of them. Further, (13) in the above-mentioned (12), the medicine may be an acetylcholinesterase inhibitor; (14) in the above-mentioned (12), the medicine may be an agent for treating, preventing or improving senile dementia, cerebrovascular dementia or attention deficit hyperactivity disorder; and (15) in the above-mentioned (14), the senile dementia may be Alzheimer-type senile dementia. Further, the present invention also relates to (16) a process for producing the compound described in the above (1), a salt thereof or a hydrate of them, which comprises fluorinating a 4-substituted piperidine compound represented by the formula:

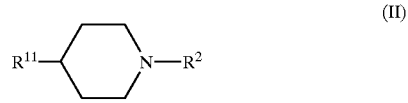

(in the formula, $R^{11}$ represents any one of group selected from the group consisting of the following substituents:

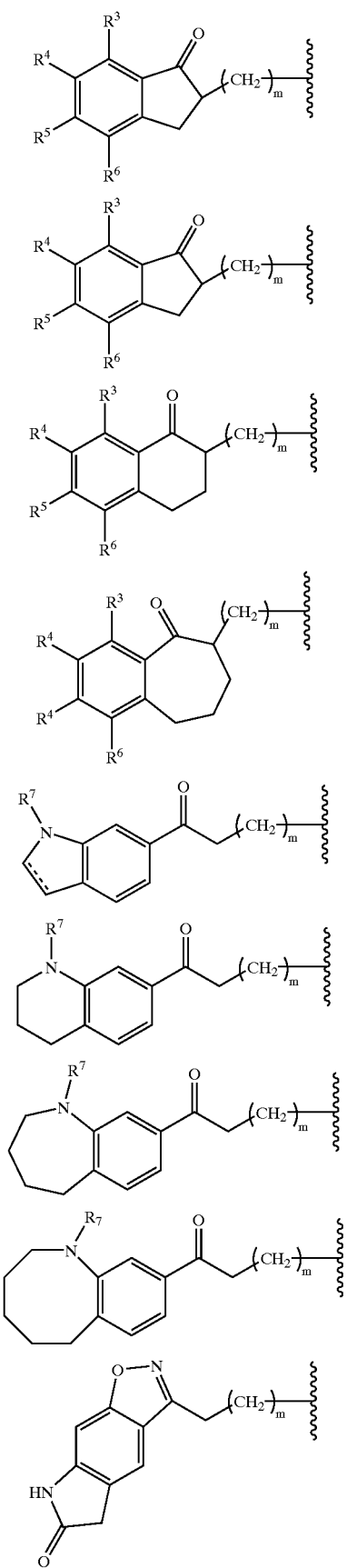
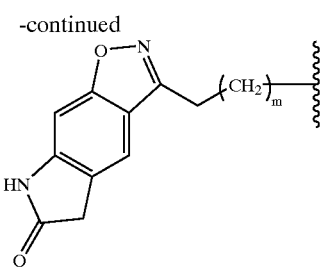
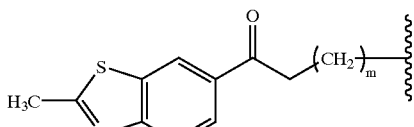
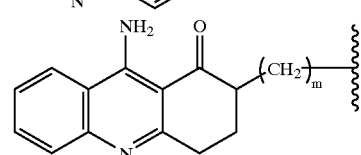
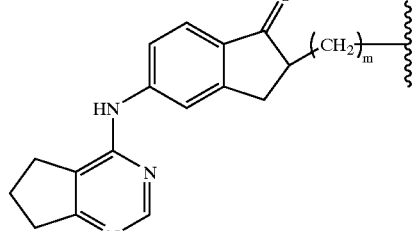
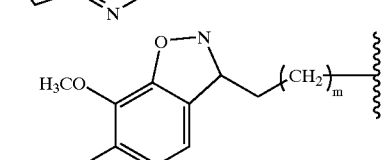
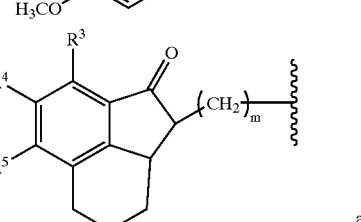
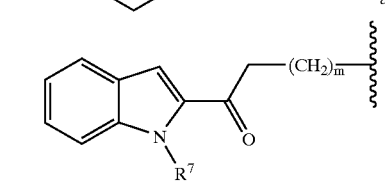

and

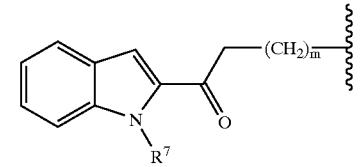

(wherein, $R^3$, $R^4$, $R^5$, $R^6$, $R^7$, m, p and a bond represented by the partial structure ⚌ have the same meanings as defined in the above (1), respectively); and $R^2$ has the same meaning as defined in the above (1)); and, if necessary, converting it into a salt; and (17) in the producing process described in the above-mentioned (16), the fluorinating agent may be N-fluorobenzenesulfoneimide, 3-cyclohexyl-2-fluoro-2,3-dihydro-3-methyl-1,1-dioxide-1,2-benzisothiazole or 2-fluoro-3,3-dimethyl-2,3-dihydro-1,2-benzisothiazole-1,1-dioxide.

The present invention provides a method for preventing, treating or improving a disease against which an acetylcholinesterase inhibitory action is efficacious, by administering a pharmacologically effective dose of the compound represented by the above-mentioned formula (I), a salt thereof or a hydrate of them to a patient.

The present invention provides use of the compound represented by the above-mentioned formula (I), a salt thereof or a hydrate of them, for producing an agent for preventing, treating or improving a disease against which an acetylcholinesterase inhibitory action is efficacious.

In the present invention, those diseases against which an acetylcholinesterase inhibitory action is efficacious include senile dementia such as Alzheimer-type senile dementia, cerebrovascular dementia and attention deficit hyperactivity disorder.

DETAILED DESCRIPTION OF THE INVENTION

Hereinafter, the symbols, terms etc. used in the present specification are explained and the present invention is illustrated in more detail.

In the present specification, the structural formula of a compound may represent a certain isomer for the sake of convenience, however, the present invention includes isomers such as all geometric isomers resulted from the structure of the compound, optical isomers due to asymmetric carbon, stereo isomers and tautomers, and a mixture of isomers. Further, it is not limited to the description of the formula given for the sake of convenience, and maybe either one of isomers or a mixture thereof. Accordingly, the compound of the present invention may contain an asymmetric carbon atom in molecule so that an optical active compound and a racemic compound may be present. However, the present invention is not limited thereto, but includes any of them. Further, crystal polymorphism may be present. However, the present invention is not limited thereto, but any of crystal forms may be single or a mixture of crystal forms. The compound (I) according to the present invention or a salt thereof may be either an anhydride or a hydrate, and any of these are included in the scope of claims of the present invention. The metabolite generated by decomposing the compound (I) according to the present invention in vivo, and the prodrug of the compound (I) of the present invention or a salt thereof are also included in the scope of claims of the present invention.

Definition of $R^1$

In the definition of $R^1$ in the above formula (I) "halogen atoms" represented by $R^3$, $R^4$, $R^5$ and $R^6$ mean, for example, fluorine atoms, chlorine atoms, bromine atoms and iodine atoms, and preferably fluorine atoms, chlorine atoms and bromine atoms.

The "hydrocarbon groups" in "optionally substituted hydrocarbon groups" represented by $R^3$, $R^4$, $R^5$ and $R^6$ mean chain hydrocarbon groups such as $C_{1-6}$ alkyl groups or cyclic hydrocarbon groups such as $C_{3-8}$ cycloalkyl groups. The "$C_{1-6}$ alkyl groups" represented by $R^3$, $R^4$, $R^5$, $R^6$ and $R^7$ mean alkyl groups having 1 to 6 carbon atoms, and for example, linear or branched alkyl groups, such as methyl group, ethyl group, n-propyl group, iso-propyl group, n-butyl group, iso-butyl group, tert-butyl group, n-pentyl group, iso-pentyl group, neopentyl group, hexyl group, 1-methylpropyl group, 1-methylbutyl group or 2-methylbutyl group may be proposed.

The "$C_{3-8}$ cycloalkyl groups" represented by $R^3$, $R^4$, $R^5$ and $R^6$ mean cyclic alkyl groups having 3 to 8 carbon atoms. For example, cyclopropyl group, cyclobutyl group, cyclopentyl group, cyclohexyl group, cycloheptyl group, cyclooctyl group etc. may be proposed.

The "$C_{1-6}$ cycloalkoxy groups" represented by $R^3$, $R^4$, $R^5$ and $R^6$ mean groups in which the group having the same meaning as the "$C_{1-6}$ alkyl group" defined above is bound to an oxygen atom. For example, linear or branched alkoxy groups such as methoxy group, ethoxy group, n-propoxy group, iso-propoxy group, n-butoxy group, iso-butoxy group, tert-butoxy group, pentyloxy group or hexyloxy group may be proposed.

The "$C_{1-6}$ alkoxyalkoxy groups" represented by $R^3$, $R^4$, $R^5$ and $R^6$ mean groups in which the "$C_{1-6}$ alkoxy group" is further bound to the group having the same meaning as the $C_{1-6}$ alkyl group defined above. For example, methoxymethoxy group, methoxyethoxy group, methoxypropoxy group, ethoxymethoxy group, ethoxyethoxy group, ethoxypropoxy group, propoxypropoxy group etc. may be proposed.

The "halogenated $C_{1-6}$ alkyl groups" represented by $R^3$, $R^4$, $R^5$ and $R^6$ mean groups in which one or not less than two halogen atoms that are the same as or different from each other are bound to the "$C_{1-6}$ alkyl group" having the same meaning as the $C_{1-6}$ alkyl group defined above. For example, chloromethyl group, dichloromethyl group, trichloromethyl group, fluoromethyl group, difluoromethyl group, trifluoromethyl group and fluoroethyl group, difluoroethyl group, trifluoroethyl group etc. may be proposed.

The "hydroxy-$C_{1-6}$ alkyl groups" represented by $R^3$, $R^4$, $R^5$ and $R^6$ mean groups in which one or not less than two hydroxyl groups are bound to the group having the same meaning as the $C_{1-6}$ alkyl group defined above. For example, hydroxymethyl group, hydroxyethyl group, 2,3-dihydroxypropyl group etc. may be proposed.

The "cyano $C_{1-6}$ alkyl groups" represented by $R^3$, $R^4$, $R^5$ and $R^6$ mean groups in which one or not less than two cyano groups are bound to the group having the same meaning as the $C_{1-6}$ alkyl group defined above. Specific examples thereof include cyanomethyl group, cyanoethyl group and cyanopropyl group.

The "halogenated $C_{1-6}$ alkoxy groups" represented by $R^3$, $R^4$, $R^5$ and $R^6$ mean groups in which the "halogenated $C_{1-6}$ alkyl group" having the same meaning as the halogenated $C_{1-6}$ alkyl group defined above is bound to an oxygen atom, the "hydroxy $C_{1-6}$ alkoxy groups" mean groups in which the "hydroxy $C_{1-6}$ alkyl group" having the same meaning as the hydroxy $C_{1-6}$ alkyl group defined above is bound to an oxygen atom, and the "cyano $C_{1-6}$ alkoxy groups" mean groups in which the "cyano $C_{1-6}$ alkyl group" having the same meaning as the cyano $C_{1-6}$ alkyl group defined above is bound to an oxygen atom.

The "$C_{1-6}$ acyl groups" represented by $R^3$, $R^4$, $R^5$ and $R^6$ mean linear or branched acyl groups derived from fatty acids having 1 to 6 carbon atoms. For example, formyl group, acetyl group, propionyl group, butyryl group, isobutyryl group, valeryl group, isovaleryl group, pivaloyl group and hexanoyl group may be proposed.

The "optionally substituted amino groups" represented by $R^3$, $R^4$, $R^5$ and $R^6$ mean amino groups in which the nitrogen atom may be substituted with a group such as a $C_{1-6}$ alkyl group, and the amino groups also include cyclic amino groups. As the "optionally substituted amino groups", for example, amino group (—$NH_2$), methyl amino group (—$NHCH_3$), dimethyl amino group (—$N(CH_3)_2$), pyrrolidinyl group, pyrazolinyl group, piperidyl group and piperazinyl group may be proposed.

The "optionally substituted amide groups" represented by $R^3$, $R^4$, $R^5$ and $R^6$ mean amide groups in which the nitrogen atom may be substituted with a group such as a $C_{1-6}$ alkyl group, and the amide groups also include amide groups of cyclic amine. As the "optionally substituted amide groups", for example, amide group (—$CONH_2$), N-methylamide group (—CONHCH$_3$), N,N-dimethylamide group (—CON(CH$_3$)$_2$), N-ethylamide group (—CONHC$_2$H$_5$), N,N-diethylamide group (—CON(C$_2$H$_5$)$_2$), N-methyl-N-ethylamide group (—CON(CH$_3$)C$_2$H$_5$), pyrrolidinylcarbonyl group, pyrazolinylcarbonyl group, piperidylcarbonyl group and piperazinylcarbonyl group may be proposed.

The "C$_{1-6}$ thioalkoxy groups" represented by R$^3$, R$^4$, R$^5$ and R$^6$ mean groups in which the group having the same meaning as the C$_{1-6}$ alkyl group defined above is bound to a sulfur atom. For example, methylthio group (—SCH$_3$) and ethylthio group (—SC$_2$H$_5$) may be proposed.

In the definition of R$^1$ in the above formula (I), symbol m indicates 0 or an integer from 1 to 6, and m is preferably 0 or an integer from 1 to 5, more preferably 0 or an integer from 1 to 3, further preferably 0 or an integer of 1 or 2, and the most preferably 0 or 1. Moreover, symbol p represents an integer of 1 or 2, and preferably 1.

In the above formula (I), R$^1$ may be any group selected from the group consisting of the groups shown below:

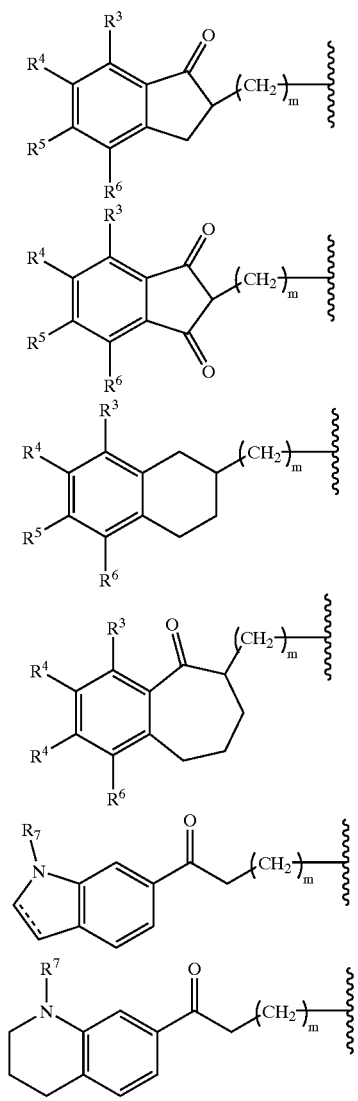

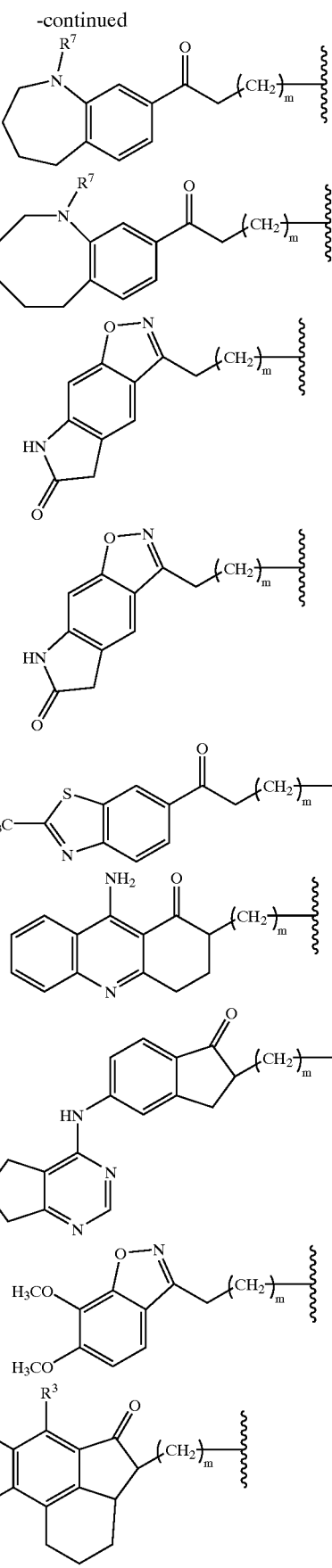

and

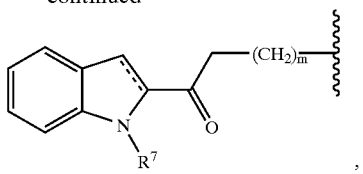

and preferably a group represented by the formula:

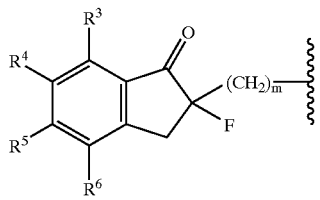

in the formula, $R^3$, $R^4$, $R^5$ and $R^6$ and m have the same meanings as defined above. In this case, preferably, $R^3$, $R^4$, $R^5$ and $R^6$ are the same as or different from each other and each represents a hydrogen atom, a halogen atom, a hydroxyl group, a $C_{1-6}$ alkyl group, a $C_{1-6}$ alkoxy group, a halogenated $C_{1-6}$ alkyl group, a hydroxy $C_{1-6}$ alkyl group, a cyano $C_{1-6}$ alkyl group, a halogenated $C_{1-6}$ alkoxy group, a hydroxy $C_{1-6}$ alkoxy group, a cyano $C_{1-6}$ alkoxy group; and m is 0 or an integer from 1 to 5. More preferably, $R^3$, $R^4$, $R^5$ and $R^6$ are the same as or different from each other and each represents a hydrogen atom, a $C_{1-6}$ alkoxy group, a halogenated $C_{1-6}$ alkoxy group, a hydroxy $C_{1-6}$ alkoxy group or a cyano $C_{1-6}$ alkoxy group; and m is 0 or an integer from 1 to 3. Further preferably, $R^3$, $R^4$, $R^5$ and $R^6$ are the same as or different from each other and each represents a hydrogen atom or a $C_{1-6}$ alkoxy group (for example, a methoxy group, ethoxy group, n-propoxy group and i-propoxy group); and m is 1 or 2. The most preferably, $R^3$ and $R^6$ are hydrogen atoms; $R^4$ and $R^5$ are $C_{1-6}$ alkoxy groups which are the same as or different from each other (for example, methoxy group, ethoxy group, n-propoxy group and i-propoxy group); and m is 1 or 2. As $R^1$, [(5,6-dimethoxy-2-fluoro-1-indanon)-2-yl] methyl group is the most preferred.

Definition of $R^2$

In the above formula (I), the "$C_{1-6}$ alkyl groups" in the "optionally substituted $C_{1-6}$ alkyl groups" represented by $R^2$ have the same meaning as the $C_{1-6}$ alkyl group defined above. For example, linear or branched alkyl groups such as methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 2-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group or 3-methylpentyl group, and preferably, methyl group, ethyl group, n-propyl group, i-propyl group, 2-methyl-1-propyl group and t-butyl group may be proposed.

The "$C_{2-6}$ alkenyl groups" in the "optionally substituted $C_{2-6}$ alkenyl groups" represented by $R^2$ refer to alkenyl groups having 2 to 6 carbon atoms. For example, linear or branched $C_{2-6}$ alkenyl groups such as vinyl group, allyl group, 1-propenyl group, isopropenyl group, 1-buten-1-yl group, 1-buten-2-yl group, 1-buten-3-yl group, 2-buten-1-yl group or 2-buten-2-yl group, and preferably, vinyl group, allyl group and isopropenyl group may be proposed.

The "$C_{2-6}$ alkynyl groups" in the "optionally substituted $C_{2-6}$ alkynyl groups" represented by $R^2$ refer to alkynyl groups derived from alkyne having 2 to 6 carbon atoms. For example, linear or branched $C_{2-6}$ alkynyl groups such as ethynyl group, 1-propynyl group, 2-propynyl group, butynyl group, pentynyl group and hexynyl group.

As the "substituent" in the "optionally substituted $C_{1-6}$ alkyl groups", "optionally substituted $C_{2-6}$ alkenyl groups" and "optionally substituted $C_{2-6}$ alkynyl groups" represented by $R^2$, for example, a halogen atom, a hydroxyl group, a nitrile group, a $C_{1-6}$ alkyl group, $C_{3-8}$ cycloalkyl group, a $C_{1-6}$ alkoxy group, a $C_{1-6}$ alkoxyalkoxy group, an aryloxy group, an aralkyloxy group, a halogenated $C_{1-6}$ alkyl group, a hydroxy $C_{1-6}$ alkyl group, a cyano $C_{1-6}$ alkyl group, a halogenated $C_{1-6}$ alkoxy group, a hydroxy $C_{1-6}$ alkoxy group, a cyano $C_{1-6}$ alkoxy group, a $C_{1-6}$ acyl group, a nitro group, an optionally substituted amino group, an optionally substituted amide group, a mercapto group and a $C_{1-6}$ thioalkoxy group, and preferably a halogen atom, a hydroxyl group and a nitrile group may be proposed.

The "substituents" such as "halogen atom", "$C_{1-6}$ alkyl group", "$C_{3-8}$ cycloalkyl group", "$C_{1-6}$ alkoxy group", "$C_{1-6}$ alkoxyalkoxy group", "halogenated $C_{1-6}$ alkyl group", "hydroxy $C_{1-6}$ alkyl group", "cyano $C_{1-6}$ alkyl group", "halogenated $C_{1-6}$ alkoxy group", "hydroxy $C_{1-6}$ alkoxy group", "cyano $C_{1-6}$ alkoxy group", "$C_{1-6}$ acyl group", "optionally substituted amino group", "optionally substituted amide group", "mercapto group" or "$C_{1-6}$ thioalkoxy group" have the same meanings as defined above, respectively. Moreover, the "aryl group" in the above-mentioned "aryloxy group" means a cyclic hydrocarbon group constituting an aromatic ring. For example, monocyclic, dicyclic or tricyclic aryl groups such as a phenyl group, an indenyl group, a naphthyl group, an azulenyl group, a heptalenyl group, an anthnyl group or a phenanthrenyl group may be proposed. The "aryloxy group" means a group in which the above-mentioned aryl group is bound to an oxygen atom. For example, a phenoxy group and naphthyloxy group may be proposed. The above-mentioned "aralkyloxy group" means a group in which a group having the same meaning as the above-mentioned aryl group is bound to a $C_{1-6}$ alkyl group, and the resulting arylalkyl group is further bound to an oxygen atom. For example, a benzyloxy group, a phenylethoxy group, a phenylpropoxy group and naphthylmethoxy group may be proposed.

As $R^2$, preferably a hydrogen atom or an optionally substituted $C_{1-6}$ alkyl group, more preferably a hydrogen atom or a methyl group, ethyl group, n-propyl group, iso-propyl group, 2-methyl-1-propyl group and tert-butyl group which may be respectively substituted, and further preferably a hydrogen atom may be proposed.

The above description has discussed the definitions of $R^1$ and $R^2$, and $R^1$ and $R^2$ may be independent of each other and each may be a group based upon the respective definitions, and it goes without saying that the combination thereof is not limited. As the more preferable mode of the compound (I) of the present invention, the case where $R^1$ is a group represented by the formula:

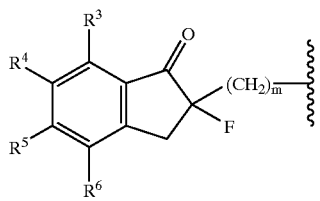

(in the formula, each symbol has the same meaning as defined above); and $R^2$ is a hydrogen atom or an optionally substituted $C_{1-6}$ alkyl group may be proposed. As the further preferable mode, the case where $R^1$ is a 5,6-dimethoxy-2-fluoro-1-indanon-2-yl group; and $R^2$ is a hydrogen atom or a methyl group, ethyl group, n-propyl group, iso-propyl group, 2-methyl-1-propyl group or t-butyl group which may be substituted, respectively may be proposed. As the most preferable mode, the case where $R^1$ is 5,6-dimethoxy-2-fluoro-1-indanon-2-yl group; and $R^2$ is a hydrogen atom may be proposed. As the most preferable mode of the compound (I) of the present invention, for example, any compound selected from 4-[(5,6-dimethoxy-2-fluoro-1-indanon)-2-yl]methylpiperidine, 4-[(5,6-dimethoxy-2-fluoro-1-indanon)-2-yl]methyl-1-methylpiperidine, 4-[(5,6-dimethoxy-2-fluoro-1-indanon)-2-yl]methyl-1-(1-methylethyl)piperidine and 4-[(5,6-dimethoxy-2-fluoro-1-indanon)-2-yl]methyl-1-(2-methylpropyl)piperidine may be proposed, however, it goes without saying that the present invention is not limited by them.

In the specification of the present application, the "salt" refer to a pharmacologically acceptable salt, and is not particularly limited, as long as it forms an addition salt with the compound of the present invention. For example, hydrohalogenates such as hydrofluoride, hydrochloride, hydrobromide or hydroiodide; inorganic acid salts such as sulfate, nitrate, perchlorate, phosphate, carbonate or bicarbonate; organic carboxylates such as acetate, oxalate, maleate, tartrate or fumarate; organic sulfonates such as methanesulfonate, trifluoromethanesulfonate, ethanesulfonate, benzenesulfonate, toluenesulfonate or camphor-sulfonate; amino acid salts such as aspertate or glutamate; amine salts such as trimethylamine salt, triethylamine salt, procaine salt, pyridine salt or phenethylbenzylamine salt; alkali metal salts such as sodium salt or potassium salt; and alkali earth metal salts such as magnesium salt or calcium salt, and preferably hydrochloride and oxalate may be proposed.

As the producing process of the compound of the present invention, various methods may be proposed. As the typical method, for example, the following method may be proposed. That is, the compound (I) of the present invention can be produced by fluorinating a 4-substituted piperidine compound represented by the formula (II):

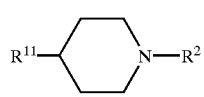
(II)

(in the formula, $R^{11}$ represents any one group selected from the following substituents:

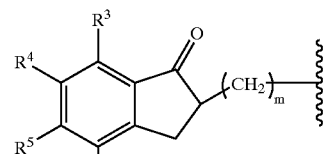
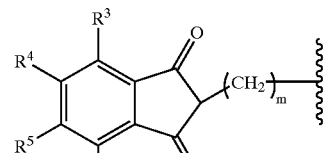
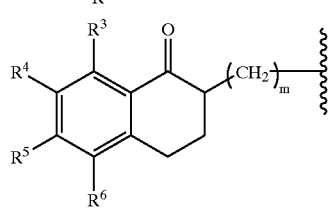
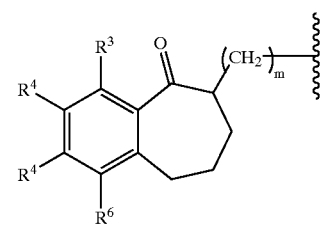
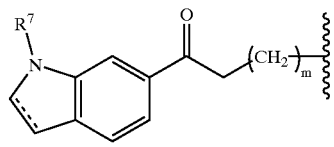
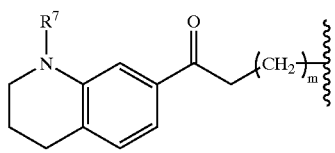
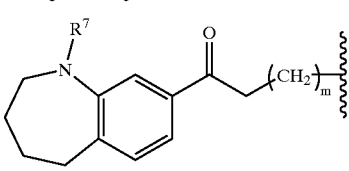
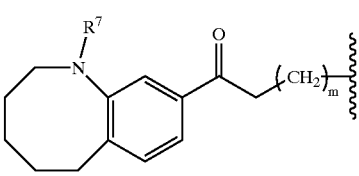
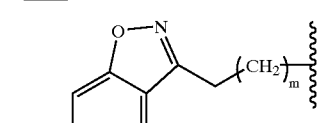
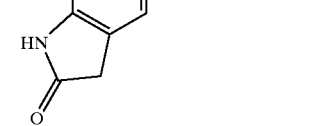

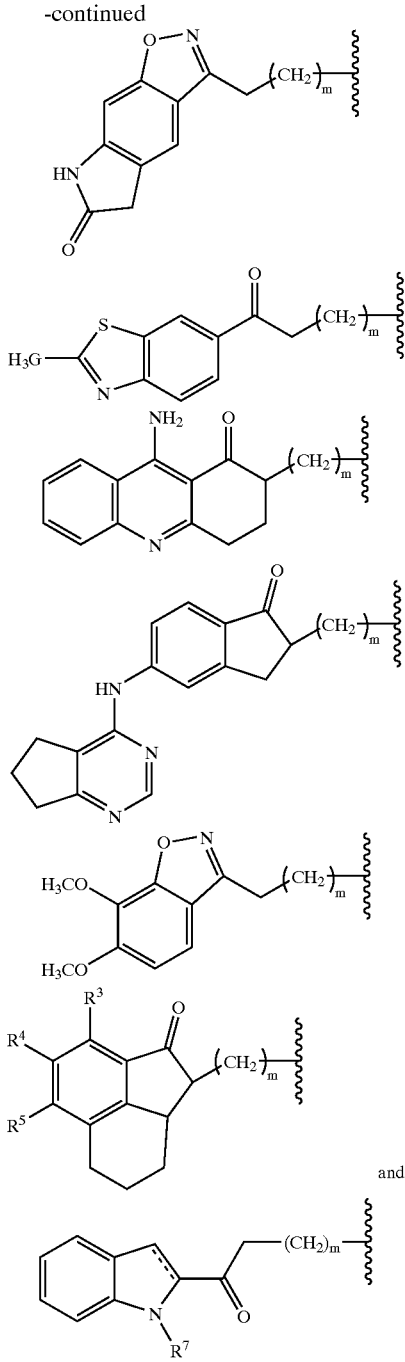

(in the formula, $R^3$, $R^4$, $R^5$, $R^6$, $R^7$, m, p and a bond represented by the partial structure ═ have the same meanings as defined above, respectively); and $R^2$ has the same meaning as defined above) and, if necessary, converting it into a salt. In the producing process, a preferable result can be obtained by reacting with a base first, and then reacting with a fluorinating agent, in general. As the base to be used, a strong base is preferable, and the kind thereof is not particularly limited. For example, lithium bis(trimethylsilyl)amide, n-butyl lithium, lithium diisopropylamide, sodium amide, sodium hydride, sodium methoxide, sodium ethoxide, potassium t-butoxide, sodium hydroxide, potassium hydroxide etc. may be proposed. As the fluorinating agent to be used, for example, N-fluorobenzenesulfonimide (NFSI, CAS Registration No: 133745-75-2), 3-cyclohexyl-2-fluoro-2,3-dihydro-3-methyl-1,1-dioxide-1,2-benzisothiazole (CMIT-F, CAS Reg. Nos: 186806-24-6, 196106-79-3), 2-fluoro-3,3-dimethyl-2,3-dihydro-1,2-benzisothiazole-1,1-dioxide (CAS Reg. No: 124170-23-6), diethylaminosulfur trifluoride (DAST, CAS Reg. No: 38078-09-0), N,N-diethyl-1,1,2,3,3,3-hexafluoropropylamine (Ishikawa Reagent), hydrogen fluoride, tetraalkylammonium fluoride, potassium fluoride, cesium fluoride, hydrogen fluoride-pyridine (Olah Reagent) etc. may be proposed. Preferably, N-fluorobenzenesulfonimide, 3-cyclohexyl-2-fluoro-2,3-dihydro-3-methyl-1,1-dioxide-1,2-benzisothiazole, 2-fluoro-3,3-dimethyl-2,3-dihydro-1,2-benzisothiazole-1,1-dioxide may be proposed. The solvent to be used is not particularly limited as long as it is inactive to the above-mentioned strong base and fluoridating agent. For example, tetrahydrofuran (THF), 1,2-dimethoxy ethane (DME, ethylene glycol dimethyl ether), ethyl ether, isopropyl ether, butyl ether, 1,3-dioxane, 1,4-dioxane, 1,3-dioxolane, benzene, toluene, xylene, cyclohexane, n-hexane, n-pentane, n-octane, petroleum ether etc. may be proposed, and these solvents may be used singly or as a mixture of two or more.

Here, the 4-substituted piperidine compound represented by the above formula (II) may be produced by the method similar to or in accordance with those described in, for example, JP-A 64-79151 (EP-A1 296560), JP-A 55-140149 (EP-A1 487071), JP-A 6-500794, JP-A 6-510788, JP-A 6-508904, JP-A 5-279355, JP-A 5-320160, JP-A 6-116237, JP-A 6-41070 etc.

Here, material compounds in the production of the compound of the present invention may be a salt and a hydrate, and are not particularly limited as long as they are inert to the reaction. Moreover, when the compound (I) of the present invention is obtained as a free form, it may be converted into a salt form that may be formed by the above-mentioned compound (I) in a conventional method. Further, various isomers of the compound (I) of the present invention (for example, geometric isomers, optical isomers due to an asymmetric carbon, stereoisomers and tautomers) can be purified and isolated by using conventional separating means such as recrystallization, a diastereomer salt method, an enzymolysis method and various chromatographies (such as thin layer chromatography, column chromatography or gas chromatography).

The compound represented by the above formula (I) of the present invention, a salt thereof or a hydrate of them may be prepared in a conventional method. As the preferable agent forms include tablets, powders, fine granules, granules, coated tablets, capsules, syrup, troche, inhalant, suppositories, injections, ointments, eye ointments, ophthalmic solutions, nasal drops, ear drops, cataplasms and lotions. In preparing, generally used fillers, binders, disintegrating agents, lubricants, coloring agents, flavoring agents, and if necessary, a stabilizer, emulsifier, absorbefacients, surfactant, pH adjusting agent, preservative, antioxidant etc. may be used. It may be prepared in a conventional method by blending components generally used as materials for pharmaceutical preparations. As these components, for example, (1) animal and vegetable oils such as soybean oil, beef tallow or synthetic glyceride; (2) hydrocarbons such as fluid paraffin, squalane or solid-paraffin; (3) ester oils such as octyldodecyl myristate or isopropyl myristate; (4) higher alcohols such as setostearyl alcohol or behenyl alcohol; (5) silicon resin; (6) silicon oil; (7) surfactants such as polyoxyethylene fatty acid ester, sorbitan fatty acid ester, glycerin fatty acid ester, polyoxyethylene sorbitan fatty acid ester, polyoxyethylene hydrogenated castor oil or polyoxyethylene-polyoxypropylene block copolymer; (8) water soluble polymers such as hydroxyethyl cellulose, polyacrylic acid, carboxyvinyl polymer, polyethylene glycol, polyvinyl pyrrolidone or methyl cellulose; (9) lower alcohols such as ethanol or isopropanol; (10) polyhydric alcohols such as glycerin, propylene glycol, dipropylene glycol or sorbitol; (11) saccharides such as glucose or saccharose; (12) inorganic powders such as silicic anhydride, aluminum magnesium silicate or aluminum silicate; (13) purified water etc. may be proposed.

1) As the fillers, for example, lactose, corn starch, saccharose, glucose, mannitol, sorbitol, crystalline cellulose, silicon dioxide etc.; 2) as the binders, for example, polyvinyl alcohol, polyvinyl ether, methyl cellulose, ethyl cellulose, gum arabic, gum tragacanth, gelatin, shellac, hydroxypropyl cellulose, hydroxypropylmethyl cellulose, polyvinyl pyrrolidone, polypropylene glycol-polyoxyethylene block polymer, megulumine, calcium citrate, dextrin, pectin etc.; 3) as the disintegrating agents, for example, starch, agar, gelatin powder, crystalline cellulose, calcium carbonate, sodium hydrogencarbonate, calcium citrate, dextrin, pectin, carboxymethyl cellulose, calcium etc.; 4) as the lubricants, for example, magnesium stearate, talc, polyethylene glycol, silica, hydrogenated vegetable oil etc.; 5) as the coloring agents, those which are permitted to add to pharmaceutical preparations; 6) as the flavoring agents, cocoa powder, menthol, aromatic powder, menthol oil, borneol, cinnamon powder etc.; and 7) as the antioxidant, ascorbic acid, α-tocopherol etc. which are permitted to add to drugs may be used, respectively.

1) Oral preparation is prepared by adding fillers and, if necessary, a binder, a disintegrating agent, a lubricant, a coloring agent, a flavoring agent etc. to the compound of the present invention or a salt thereof have been added to the compound or a salt thereof, and then it is prepared into a form of powders, fine granules, granules, tablets, coated tablets, capsules etc., in a conventional method. 2) In the case of tablets and granules, these may of course be sugar-coated, gelatin-coated and other, if necessary. 3) In the case of liquid preparations such as syrup, injection, eye ointments etc., a pH adjusting agent, a dissolving agent and an isotonic agent etc. and, if necessary, a solubilizer, a stabilizer, a buffer, a suspending agent, an antioxidant etc. are added, and then prepared in a conventional method. In preparing the liquid, it may be prepared as a freeze drying product, and the injection may be administered intravenously, subcutaneously and by intramascular injection. Preferable examples of the suspending agent include methyl cellulose, polysorbate 80, hydroxyethyl cellulose, gum arabic, tragacanth powder, sodium carboxymethyl cellulose, polyoxyethylene sorbitan monolaurate etc.; preferable examples of the solubilizer include polyoxyethylene hydrogenated castor oil, polysorbate 80, nicotinamide, polyoxyethylene sorbitan monolaurate etc.; preferable examples of the stabilizer include sodium sulfite, sodium metasulfite, ether etc.; preferable examples of the preservative include methyl paraoxybenzoate, ethyl paraoxybenzoate, sorbicacid, phenol, cresol, chlorocresoletc. Further, in the case of 4) the externally applied agents, the producing process is not particularly limited, and these may be produced in a conventional method. As the base materials to be used, various materials commonly used in drugs, quasi-drugs, cosmetics, etc. may be used. For example, base materials such as animal and vegetable oils, mineral oils, ester oils, waxes, higher alcohols, fatty acids, silicone oil, surfactants, phospholipids, alcohols, polyhydric alcohols, water-soluble polymers, clay minerals or purified water may be proposed, and if necessary, pH adjusting agents, antioxidants, chelating agents, preservatives, coloring agents, flavoring agents etc. may be added thereto. Moreover, if necessary, components having a differentiation inducing effect, bloodstream promoting agents, germicides, antiphlogistics, cell activators, vitamins, amino acids, moisturizers, keratin solubilizers etc. may also be added.

The dose of the medicament according to the present invention varies depending on the degree of symptoms, age, sex, weight, administration form, kind of salt, difference in sensitivity to the medicine, specific type of the disease and the like, and in case of an adult, it is orally administered in amount of generally 30 μg to 1000 mg, preferably 100 μg to 500 mg and more preferably 100 μg to 100 mg, and approximately 1 to 3000 μg/kg, preferably 3 to 1000 μg/kg in the case of injection administration, at one time or in several portions per day.

The present invention makes it possible to provide a novel compound represented by the above formula (I), a salt thereof and an hydrate of them. The compound represented by the above-mentioned formula (I) of the present invention, a salt thereof or a hydrate of them exhibits a superior acetylcholinesterase inhibitory action. Therefore, it is useful as an agent for treating, preventing or improving various senile dementia, cerebrovascular dementia or attention deficit hyperactivity disorder, and is especially useful as an agent for treating, preventing or improving Alzheimer-type senile dementia.

EXAMPLES

The best mode of the compound according to the present invention represented by the above formula (I) or a salt thereof are shown below. The following Reference Examples, Examples and Test Examples are exemplary, and the compound of the present invention or a salt thereof is not limited to the following specific examples in any case. One skilled in the art may make various variations of theses specific examples and claims of the present invention to carry out the present invention. Further, these variations are included in the scope of the claims of the present invention.

Example 1

4-[(5,6-Dimethoxy-2-fluoro-1-indanon)-2-yl]methylpiperidine hydrochloride

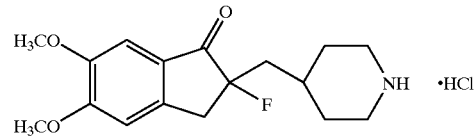

In 5 ml of 1,2-dichloroethane was dissolved 0.25 g (0.63 mmol) of 1-benzyl-4-[(5,6-dimethoxy-2-fluoro-1-indanon)-2-yl]methylpiperidine, followed by adding 0.81 ml (0.77 mmol) of 1-chloroethylchloroformate. After heating under reflux for one hour, it was evaporated. 5 ml of methanol was added thereto, followed by heating under reflux for further 40 minutes. It was evaporated, and the resulting residue was recrystallized from methanol-diethyl ether, to obtain 0.19 g of the title compound (free form) as pale yellowish white crystals (yield; 98%). The physicochemical data of the free form of the title compound are shown below.

Melting point: 234–238° C. (decomposition)

$^1$H-NMR (400 Mz:CD$_3$OD) δ 1.45–1.60 (2H, m), 1.77 (1H, ddd, J=6 Hz, J=14.8 Hz, J=30 Hz), 1.94–2.14 (4H, m), 2.94–3.06 (2H, m), 3.22–3.48 (4H, m), 3.86 (3H, s), 3.95 (3H, s), 7.07 (1H, s), 7.18 (1H, s).

The product was converted into hydrochloride in a conventional method and recrystallized from 95% ethanol/tert-butylmethyl ether, to give the title compound as pale yellowish white crystals. The physicochemical data of the title compound (hydrochloride) are shown below.

Melting point: >240° C. (decomposition)

$^1$H-NMR (400 Mz:CDCl$_3$) δ 1.72–2.17 (7H, m), 2.91 (1H, bs), 3.19–3.39 (2H, m), 3.48 (2H, bs), 3.92 (3H, s), 3.99 (3H, s) 6.84 (1H, s), 7.18 (1H, s), 9.31 (1H, bs), 9.56 (1H, s).

ESI-MS:m/z=308 (M+H$^+$)

Example 2

4-[(5,6-Dimethoxy-2-fluoro-1-indanon)-2-yl]methyl-1-methylpiperidine hydrochloride

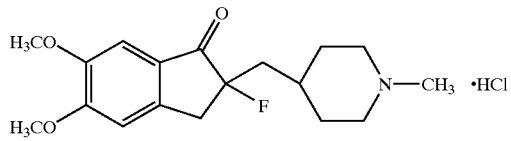

To 68 mg (0.20 mmol) of 4-[(5,6-dimethoxy-2-fluoro-1-indanon)-2-yl]methylpiperidine hydrochloride were added 0.052 ml (1.39 mmol) of formic acid and 0.10 ml (1.38 mmol) of 37% formaldehyde. After heating at 80° C. for 3 hours, it was allowed to be cooled to room temperature and 30 ml of ethyl acetate was added thereto. It was washed with 30 ml of aqueous 1N sodium hydroxide and 30 ml of brine, dried (MgSO$_4$) and then evaporated. The resulting residue was purified by using fractionating thin layer chromatography (methylene chloride/methanol), to give 34 mg of the title compound (free form) as a pale yellow oil (yield; 53%). The product was converted into hydrochloride in a conventional method and recrystallized from ethanol/tert-butylmethyl ether, to five the title compound as pale yellowish white crystals. The physicochemical data of the title compound (hydrochloride) are shown below.

Melting point: 215–220° C. (decomposition)

$^1$H-NMR (400 Mz:CDCl$_3$) δ: 1.80–2.27 (7H, m), 2.72–2.86 (2H, m), 2.80 (3H, s), 3.23 (1H, dd, J=9.6 Hz, J=16.8 Hz), 3.32 (1H, dd, J=17.6 Hz, J=38.4 Hz), 3.53 (2H, t, J=12.8 Hz), 3.92 (3H, s), 4.00 (3H, s), 6.85 (1H, s), 7.17 (1H, s). (No protons of hydrochloric acid were observed).

ESI-MS:m/z=322 (M+H$^+$).

Example 3

4-[(5,6-Dimethoxy-2-fluoro-1-indanon)-2-yl]methyl-1-(1-methylethyl)piperidine hydrochloride

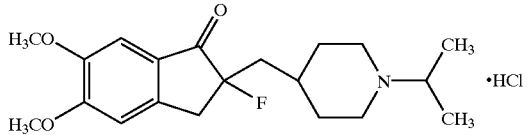

In 3 ml of DMF was dissolved 50 mg (0.15 mmol) of 4-[(5,6-dimethoxy-2-fluoro-1-indanon)-2-yl]methylpiperidine hydrochloride, followed by adding 0.049 ml (0.35 mmol) of triethylamine and 0.016 ml (0.17 mmol) of 2-bromopropane. After heating at 70° C. for 6 hours, it was allowed to be cooled to room temperature and 30 ml of ethyl acetate was added thereto. It was washed with 30 ml of water and 30 ml of brine, dried (MgSO$_4$) and then evaporated. The resulting residue was purified by a fractionating thin layer chromatography (methylene chloride/methanol), to give 13 mg of the title compound (free form) as a pale yellow oil (yield; 26%). The product was converted into hydrochloride in a conventional method and solidified by using diethyl ether, to give the title compound as a pale yellowish white amorphous. The physicochemical data of the title compound (hydrochloride) are shown below.

$^1$H-NMR (400 Mz:CDCl$_3$) δ: 1.43 (6H, d, J=5.6 Hz), 1.81 (1H, bd, J=12.8 Hz), 1.90–1.95 (1H, m), 1.96–2.01 (1H, m), 2.07–2.32 (4H, m), 2.69–2.86 (2H, m), 3.18–3.50 (5H, m), 3.92 (3H, s), 3.99 (3H, s), 6.84 (1H, s), 7.17 (1H, s), 11.55 (1H, bs).

ESI-MS:m/z=350 (M+H$^+$)

Example 4

4-[(5,6-Dimethoxy-2-fluoro-1-indanon)-2-yl]methyl-1-(2-methylpropyl)piperidine hydrochloride

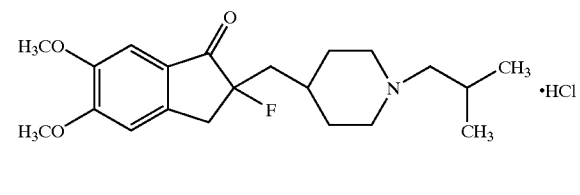

In the same manner as in Example 3, the title compound (free form) was obtained as a pale yellow oil (yield; 40%). The product was converted into hydrochloride in a conventional method and recrystallized from ethanol/tert-butylmethyl ether, to give the title compound as pale yellowish white crystals. The physicochemical data are shown below.

Melting point: 220–225° C. (decomposition)

$^1$H-NMR(400 Mz:CDCl$_3$) δ: 1.15 (6H, d, J=6.8 Hz), 1.78 (1H, bd, J=13.2 Hz), 1.93 (1H, bs), 1.99 (1H, bs), 2.08–2.40 (5H, m), 2.62–2.78 (2H, m), 2.80 (2H, d, J=6.4 Hz), 3.23 (1H, dd, J=9.6 Hz, J=16.8 Hz), 3.31 (1H, dd, J=17.6 Hz, J=38.8 Hz), 3.58 (2H, bt, J=14 Hz), 3.92 (3H, s), 3.99 (3H, s), 6.84 (1H, s), 7.17 (1H, s), 11.61 (1H, bs).

ESI-MS:m/z=364 (M+H$^+$).

Hereinbelow, a pharmacological test example is shown to illustrate the usefulness of the compound of the present invention as a medicament.

Inhibitory Effect on Acetylcholinesterase in vitro

Using a rat brain homogenate as a source of acetylcholinesterase, the esterase activity was determined in accordance with the method of Ellman et al[1].

[1]; Ellman, G. L., Courtney, K. D., Andres, V. and Featherstone, R. M., (1961), Biochem.Pharmacol., 7, 88 to 95.

Acethylthiocholine (as a substrate), a test compound and DTNB (5,5'-dithiobis(2-nitrobenzoic acid)) were added to the mouse brain homogenate, and then incubated. Then, the resulting yellow product produced by the reaction of the resulting thiocholine with DTNB was determined for the change in absorbance at 412 nm, to determine the acetylcholinesterase activity. The acetylcholinesterase inhibitory action of each test compound was determined in terms of 50% inhibitory concentration (IC$_{50}$). Here, the test compounds were respectively dissolved in physiological saline, and used.

In the above-mentioned test examples, the compound represented by the above-mentioned formula (I) of the present invention, a salt thereof or a hydrate of them showed significant acetylcholinesterase inhibitory actions.

What is claimed is:

1. A compound, a salt thereof, or a hydrate of said compound or salt thereof, said compound represented by the formula:

 (I)

wherein $R^2$ of formula (I) represents a hydrogen atom, an optionally substituted $C_{1-6}$ alkyl group, an optionally substituted $C_{2-6}$ alkenyl group or an optionally substituted $C_{2-6}$ alkynyl group, a salt thereof, or a hydrate of said compound or salt thereof;

$R^1$ is a group selected from the group of formulae consisting of

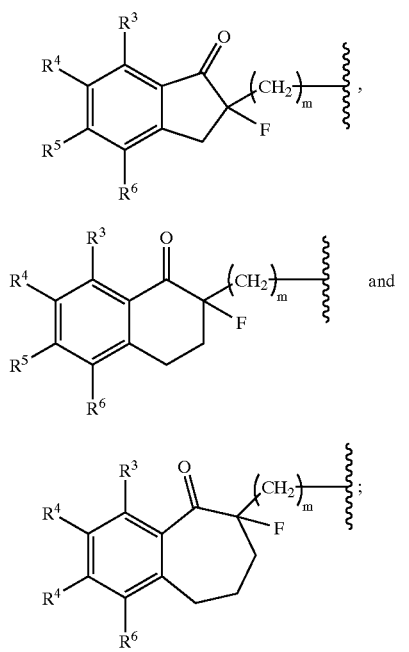

$R^3$, $R^4$, $R^5$ and $R^6$ are the same as or different from each other and each represents a hydrogen atom, a halogen atom, a hydroxyl group, an optionally substituted hydrocarbon group, an optionally substituted $C_{1-6}$ alkoxy group, a $C_{1-6}$ acyl group, a nitro group, an optionally substituted amino group, an optionally substituted amide group, a mercapto group or a $C_{1-6}$ thioalkoxy group; and m is 0 or an integer from 1 to 6.

2. The compound a salt thereof, or a hydrate of said compound or salt thereof according to claim 1, wherein said substituent in the optionally substituted $C_{1-6}$ alkyl group, optionally substituted $C_{2-6}$ alkenyl group or optionally substituted $C_{2-6}$ alkynyl group of $R^2$ is at least one selected from the group consisting of a halogen atom, a hydroxyl group, a nitrile group, a $C_{1-6}$ alkyl group, $C_{3-8}$ cycloalkyl group, a $C_{1-6}$ alkoxy group, a $C_{1-6}$ alkoxyalkoxy group, an aryloxy group, an aralkyloxy group, a halogenated $C_{1-6}$ alkyl group, a hydroxy $C_{1-6}$ alkyl group, a cyano $C_{1-6}$ alkyl group, a halogenated $C_{1-6}$ alkoxy group, a hydroxy $C_{1-6}$ alkoxy group, a cyano $C_{1-6}$ alkoxy group, a $C_{1-6}$ acyl group, a nitro group, an optionally substituted amino group, an optionally substituted amide group, a mercapto group and a $C_{1-6}$ thioalkoxy group.

3. The compound according to claim 1, or 2, a salt thereof, or a hydrate of said compound or salt thereof, wherein $R^3$, $R^4$, $R^5$ and $R^6$ are the same as or different from each other and each represents a hydrogen atom or an optionally substituted $C_{1-6}$ alkoxy group.

4. The compound according to claim 1 or 2, a salt thereof, or a hydrate of said compound or salt thereof, wherein $R^3$, $R^4$, $R^5$ and $R^6$ are the same as or different from each other and each represents a hydrogen atom or an optionally substituted methoxy group.

5. The compound according to claim 1 or 2, a salt thereof, or a hydrate of said compound or salt thereof, wherein m is an integer of 1.

6. The compound according to claim 2, a salt thereof, or a hydrate of said compound or salt thereof, wherein $R^1$ is a [(5,6-dimethoxy-2-fluoro-1-indanon)-2-yl]methyl group.

7. The compound according to claim 1 or 2, a salt thereof, or a hydrate of said compound or salt thereof, wherein $R^2$ is a hydrogen atom.

8. The compound according to claim 1 or 2, a salt thereof, or a hydrate of said compound or salt thereof, wherein $R^2$ is an optionally substituted $C_{1-6}$ alkyl group.

9. The compound according to claim 1 or 2, a salt thereof, or a hydrate of said compound or salt thereof, wherein $R^2$ is a $C_{1-6}$ alkyl group substituted with (1) a halogen atom, (2) a hydroxyl group or (3) a nitrile group.

10. The compound according to claim 2, a salt thereof, or a hydrate of said compound or salt thereof, in which $R^2$ is a methyl group, an ethyl group, a n-propyl group, an iso-propyl group, 2-methyl-1-propyl group or a tert-butyl group.

11. The compound according to claim 2, a salt thereof, or a hydrate of said compound or salt thereof, in which the compound is 4-[(5,6-dimethoxy2-fluoro-1-indanon)-2-yl]methylpiperidine, 4-[(5,6-dimethoxy-2-fluoro-1-indanon)-2-yl]methyl-1-methylpiperidine, 4-[(5,6-dimethoxy-2-fluoro-1-indanon)-2-yl]methyl-1-(1-methylethyl)piperidine or 4-[(5,6-dimethoxy-2-fluoro-1-idanon)-2-yl]methyl-1-(2-methylpropyl)piperidine.

12. The compound according to claim 7, wherein said compound is a salt thereof.

13. The compound according to claim 8, wherein said compound is a salt thereof.

14. The compound according to claim 1, a salt thereof, or a hydrate of said compound or salt thereof, wherein said $R^1$ is the group represented by formula (A).

15. A pharmaceutical composition comprising:
a therapeutically effective amount of the compound according to claim 2, a salt thereof, or a hydrate of said compound or salt thereof; and
a pharmaceutically acceptable carrier.

16. A pharmaceutical composition comprising:
a therapeutically effective amount of the compound according to claim 1, a salt thereof, or a hydrate of said compound or salt thereof; and
a pharmaceutically acceptable carrier.

17. A process for producing the compound according to claim 1, a salt thereof, or a hydrate of said compound or salt thereof, which comprises fluorinating a 4-substituted piperidine compound represented by the formula:

wherein $R^2$ in formula (II) represents a hydrogen atom, an optionally substituted $C_{1-6}$ alkyl group, an optionally substituted $C_{2-6}$ alkenyl group or an optionally substituted $C_{2-6}$ alkynyl group, a salt thereof, or a hydrate of said compound or salt thereof; and $R^{11}$ in formula (II) represents any one of group selected from the group consisting of the formulae:

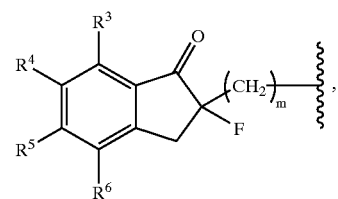

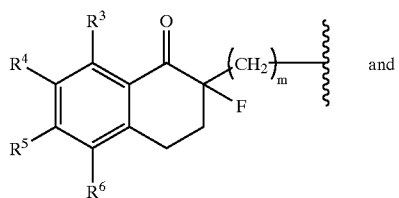

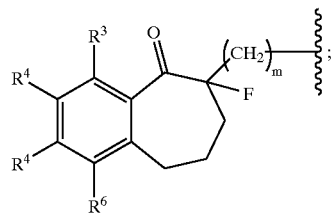

wherein $R^3$, $R^4$, $R^5$ and $R^6$ are the same as or different from each other and each represents a hydrogen atom, a halogen atom, a hydroxyl group, an optionally substituted hydrocarbon group, an optionally substituted $C_{1-6}$ alkoxy group, a $C_{1-6}$ acyl group, a nitro group, an optionally substituted amino group, an optionally substituted amide group, a mercapto group or a $C_{1-6}$ thioalkoxy group; and m is 0 or an integer from 1 to 6.

18. The producing process according to claim 17, in which the fluorinating agent is N-fluorobenzenesulfonimide, 3-cyclohexyl-2-fluoro-2,3-dihydro-3-methyl-1,1-dioxide-1,2-benzisothiazole or 2-fluoro-3,3-dimethyl-2,3-dihydro-1,2-benzisothiazole-1,1-dioxide.

19. The method of claim 17, wherein said 4-substituted piperidine compound of formula (II) is converted into a salt.

* * * * *